(12) United States Patent
Barbu et al.

(10) Patent No.: US 11,381,715 B2
(45) Date of Patent: Jul. 5, 2022

(54) COMPUTER METHOD AND APPARATUS MAKING SCREENS SAFE FOR THOSE WITH PHOTOSENSITIVITY

(71) Applicant: Massachusetts Institute of Technology, Cambridge, MA (US)

(72) Inventors: Andrei Barbu, Cambridge, MA (US); Dalitso Banda, Cambridge, MA (US); Boris Katz, Cambridge, MA (US)

(73) Assignee: MASSACHUSETTS INSTITUTE OF TECHNOLOGY, Cambridge, MA (US)

(*) Notice: Subject to any disclaimer, the term of this patent is extended or adjusted under 35 U.S.C. 154(b) by 0 days.

(21) Appl. No.: 16/450,751

(22) Filed: Jun. 24, 2019

(65) Prior Publication Data
US 2020/0021718 A1    Jan. 16, 2020

Related U.S. Application Data

(60) Provisional application No. 62/698,652, filed on Jul. 16, 2018.

(51) Int. Cl.
*H04N 5/21* (2006.01)
*G06T 7/00* (2017.01)
(Continued)

(52) U.S. Cl.
CPC .............. *H04N 5/21* (2013.01); *A61B 5/163* (2017.08); *A61B 5/369* (2021.01); *A61B 5/7267* (2013.01);
(Continued)

(58) Field of Classification Search
CPC ............ H04N 21/812; H04N 21/4532; H04N 21/2668; H04N 21/8456; H04N 21/44218;
(Continued)

(56) References Cited

U.S. PATENT DOCUMENTS 9,798,612 B1* 10/2017 Foerster ................... G06N 3/04
2012/0131611 A1* 5/2012 Yeap ................ H04N 21/42202
725/35

(Continued)

OTHER PUBLICATIONS

Harding, Graham FA, "Photosensitive epilepsy," No. 133. Cambridge University Press, 1994, 4 pages.
(Continued)

*Primary Examiner* — Samira Monshi
(74) *Attorney, Agent, or Firm* — Hamilton, Brook, Smith & Reynolds, P.C.

(57) ABSTRACT

In an embodiment, a method, and corresponding system and non-transitory computer readable medium storing instructions configured to cause a processor to execute steps are configured to introduce an auxiliary transformation to a digital media, resulting in a transformed digital media by generating the auxiliary transformation with a transform function. The method is further configured to evaluate the transformed digital media to generate a metric estimating a human response to the transformed digital media altered by the introduced auxiliary transformation. The method is further configured to train a neural network to remove the auxiliary transformation from any digital media by learning a desired transformation function from the transformed digital media and the metric associated with the transformed digital media.

27 Claims, 10 Drawing Sheets

(51) Int. Cl.
*G06T 5/00* (2006.01)
*A61B 5/16* (2006.01)
*A61B 5/00* (2006.01)
*A61B 5/369* (2021.01)

(52) U.S. Cl.
CPC ............ *G06T 5/001* (2013.01); *G06T 7/0002* (2013.01); *A61B 2503/12* (2013.01); *G06T 2207/10004* (2013.01); *G06T 2207/10016* (2013.01); *G06T 2207/20081* (2013.01); *G06T 2207/20084* (2013.01); *G06T 2207/30168* (2013.01)

(58) Field of Classification Search
CPC ......... H04N 21/25891; H04N 21/4668; H04N 21/4756; H04N 21/458; H04N 21/252
See application file for complete search history.

(56) References Cited

U.S. PATENT DOCUMENTS

| | | | |
|---|---|---|---|
| 2014/0143803 A1* | 5/2014 | Narsimhan | H04N 21/4532 725/34 |
| 2016/0360202 A1* | 12/2016 | Xu | G06N 3/084 |
| 2018/0114522 A1 | 4/2018 | Hall | |

OTHER PUBLICATIONS

Parra, J., "Photosensitivity and visually induced seizures", Current opinion in neurology, 18(2):155-159, 2005., 5 pages.
Poulsen, K., "Hackers assault epilepsy patients via computer", Wired News, 28, 2008, 2 pages.
Do, Q., "Cyber-physical systems information gathering: A smart home case study", Computer Networks, 138 (2018) 1-12.
Harding, Graham RA, "TV can be bad for your health", Nature Medicine, 4(3):265, 1998, 5 pages.
Nomura, M., et al. "A new adaptive temporal filter: Application to photosensitive seizure patients.", Psychiatry and clinical neurosciences, 54(6):685-690, 2000.
Damen, D, et al. "You-do,I-learn: Egocentric unsupervised discovery of objects and their modes of interaction towards video-based guidance.", Computer Vision and Image Understanding, 149:98-112, 2016.
Stoll, C., et al. "Navigating from a depth image converted into sound", Applied bionics and biomechanics, vol. 2015; Article ID 543492; 10 pages.
Rello , L., et al. "Good fonts for dyslexia", In Proceedings of ACM Sigaccess, p. 14; ACM, 2013.
Simon-Liedtke, J.T., et al., "Evaluating color vision deficiency daltonization methods using a behavioral visual-search method", Journal of Visual Communication and Image Representation, 35:236-247, 2016.
Pan, P., et al., "Hierarchical recurrent neural encoder for video representation with application to captioning", Proceedings of the IEEE Conference on Computer Vision and Pattern Recognition, pp. 1029-1038, 2016.
Pan, Y., et al. "Jointly modeling embedding and translation to bridge video and language", Computer Vision Foundation, 2016; 9 pages.
Siddharth, N., et al. "Seeing what you're told: Sentence-guided activity recognition in video", Proceedings of the IEEE Conference on Computer Vision and Pattern Recognition, pp. 732-739, 2014.
Kalogeiton, V., et al., "Action tubelet detector for spatio-temporal action localization", ICCV-IEEE International Conference on Computer Vision, 2017.
Baccouche, M., "Action classification in soccer videos with long short-term memory recurrent neural networks", In International Conference on Artificial Neural Networks, pp. 154-159. Springer, 2010.
Shahar, O., "Space-time super-resolution from a single video", Proceedings of the Conference on Computer Vision and Patter Recognition, pp. 3353-3360. IEEE, 2011.
Dosovitskiy, A., et al. "Flownet: Learning optical flow with convolutional networks", Proceedings of the IEEE International Conference on Computer Vision, pp. 2758-2766, 2015.
Hsieh, JT., et al., "Learning to decompose and disentangle representations for video prediction", arXiv preprint arXiv:1806.04166, 2018.
Battaglia, P., et al., "Interaction networks for learning about objects, relations and physics", Advances in neural information processing systems, pp. 4502-4510, 2016.
Gatys, L.A., "Image style transfer using convolutional neural networks", CVPR, pp. 2414-2423. IEEE, 2016.
Badrinarayanan, V., et al., "A deep convolutional encoder-decoder architecture for image segmentation.", IEEE transactions on pattern analysis and machine intelligence, 39(12):2481-2495, 2017.
Ronneberger, O., et al. "U-net: Convolutional networks for biomedical image segmentation", International Conference on Medical image computing and computer-assisted intervention, pp. 234-241. Springer, 2015.
Piergiovanni, AJ, "Learning real-world robot policies by dreaming", arXiv preprint arXiv:1805.07813, 2018.
Bousmalis, K, et al. "Using simulation and domain adaptation to improve efficiency of deep robotic grasping.", arXiv preprint arXiv:1709.07857, 2017.
Zhu,, JY, et al., "Unpaired image-to-image translation using cycle-consistent adversarial networks." IEEE International Conference on Computer Vision (ICCV), pp. 2242-2251. IEEE, 2017.
Leo, M., et al., "Computer vision for assistive technologies. Computer Vision and Image Understanding", 154:1-15, 2017.
Farringdon, J., "Visual augmented memory (VAM)", Digest of Papers. Fourth International Symposium on Wearable Computers, Oct. 2000.
Betancourt, A., et al. "The evolution of first person vision methods: A survey", IEEE Transactions on Circuits and Systems for Video Technology, 25(5):744-760, 2015.
Park, SJ, et al., "Development of image and color evaluation algorithm for the web accessibility evaluation tools", In Asia-Pacific Conference onComputer Human Interaction, pp. 389-395. Springer, 2008.
Vanderheiden., GC, "Quantification of accessibility: Guidance for more objective access guidelines", International Conference on Universal Access in Human-Computer Interaction, pp. 636-643. Springer, 2009.
Takahashi, Y, et al., "Optical filters inhibiting television-induced photosensitive seizures", Neurology, 57(10):1767-1773, 2001.
Takahashi, T, et al., "Usefulness of blue sunglasses in photosensitive epilepsy." Epilepsia, 33(3):517-521, 1992.
Blessenohl, S., "Improving indoor mobility of the visually impaired with depth-based spatial sound", Proceedings of the IEEE International Conference on Computer Vision Workshops, pp. 26-34, 2015.
Goodfellow, I., et al. "Generative adversarial nets.", Advances in neural information processing systems, pp. 2672-2680, 2014.
Dhall, A, et al., "Emotion recognition in the wild challenge 2014: Baseline, data and protocol", In Proceedings of the 16th International Conference on Multimodal Interaction, pp. 461-466. ACM, 2014.
Patraucean, V., et al. "Spatio-temporal video autoencoder with dierentiable memory", arXiv preprint arXiv:1511.06309, 2015.
World Wide Web Consortium, et al., "Web content accessibility guidelines (WCAG) 2.0.", 2008.
Fisher, R.S., et al. "Photic-and pattern-induced seizures: a review for the epilepsy foundation of America working group", Epilepsia, 46(9):1426-1441, 2005.
Takahashi, T., et al., "Photoparoxysmal response elicited by flickering dot pattern stimulation and its optimal spatial frequency of provocation", Clinical Neurophysiology, 106(1):40-43, 1998.
Wu, B., et al., "Srpgan: Perceptual generative adversarial network for single image super resolution", arXiv preprint arXiv:1712.05927, 2017.

(56) References Cited

OTHER PUBLICATIONS

Johnson, J., et al., "Perceptual losses for real-time style transfer and super-resolution." European Conference on Computer Vision, pp. 694-711. Springer, 2016.
Hochreiter, S., et al., "Long short-term memory", Neural computation, 9(8):1735-1780, 1997.
Shi, X, et al. "Convolutional lstm network: A machine learning approach for precipitation nowcasting" Advances in neural information processing systems, pp. 802-810, 2015.
He, K., et al. "Delving deep into rectifiers: Surpassing human-level performance on imagenet classification", Proceedings of the IEEE international conference on computer vision, pp. 1026-1034, 2015.
Winkler, S. "Issues in vision modeling for perceptual video quality assessment", Signal processing, 78(2):231-252, 1999.
Washington, P., et al, "A wearable social interaction aid for children with autism", Proceedings of the 2016 CHI Conference Extended Abstracts on Human Factors in Computing Systems, pp. 2348-2354. ACM, 2016.
Yamins, D., et al, "Using goal-driven deep learning models to understand sensory cortex.", Nature neuroscience, 19(3):356, 2016.
Lyons, M., et al. "The Japanese female facial expression (jae) database", Proceedings of third international conference on automatic face and gesture recognition, pp. 14-16, 1998.
Levi, G., et al., "Emotion recognition in the wild via convolutional neural networks and mapped binary patterns.", Proceedings of the 2015 ACM on international conference on multimodal interaction, pp. 503-510. ACM, 2015.
Yi, D., et al. "Learning face representation from scratch", arXiv preprint arXiv:1411.7923, 2014.
International Search Report and Written Opinion for PCT/US2019/04647 dated Oct. 25, 2019 titled "Computer Method and Apparatus Making Screens Safe for Those with Photosensitivity".
Patraucean, V., et al. "Spatio-Temporal Video Autoencoder With Differentiable Memory", Nov. 20, 2015.
Hochreiter, S., et al., "Long Short-Term Memory", Neural Computation., vol. 9, No. 8, Nov. 15, 1997.
Shi, X., et al. "Convolutional LSTM Network: A Machine Learning Approach for Precipitation Nowcasting", Sep. 19, 2015.
Leo, M., et al. "Computer vision for assistive technologies", Computer Vision and Image Understanding, Academic Press, US, vol. 154, pp. 1-15, Sep. 6, 2016.
Washington, P., et al., "Wearable Social Interaction Aid for Children with Autism", Human Factors in Computing Systems, ACM, pp. 2348-2354, May 7, 2016.
Dhall, A., et al., "Emotion Recognition In the Wild Challenge 2014", Ultimodal Interaction, ACM, pp. 461-466, Nov. 12, 2014.
Sanda, D. H., "Deep Video-to-Video Transformations for Accessibility with an Application to Photosensitivity", Sep. 30, 2018. [retrieved from the Internet: URL:https://dspace.mit.edu/bitstream/handle/1721.1/121622/1098049248-MIT.pdf?sequenc e= 1&isAllowed=y [retrieved on Oct. 16, 2019].
Barbu, A., et al., "Deep video-to-video transformations for accessibility with an application to photosensitivity", Pattern Recognition Letters, Jun. 1, 2019.
International Preliminary Report on Patentability for PCT/US2019/041647 dated Jan. 29, 2021, titled "Computer Method and Apparatus Making Screens Safe for Those with Photosensitivity".

\* cited by examiner

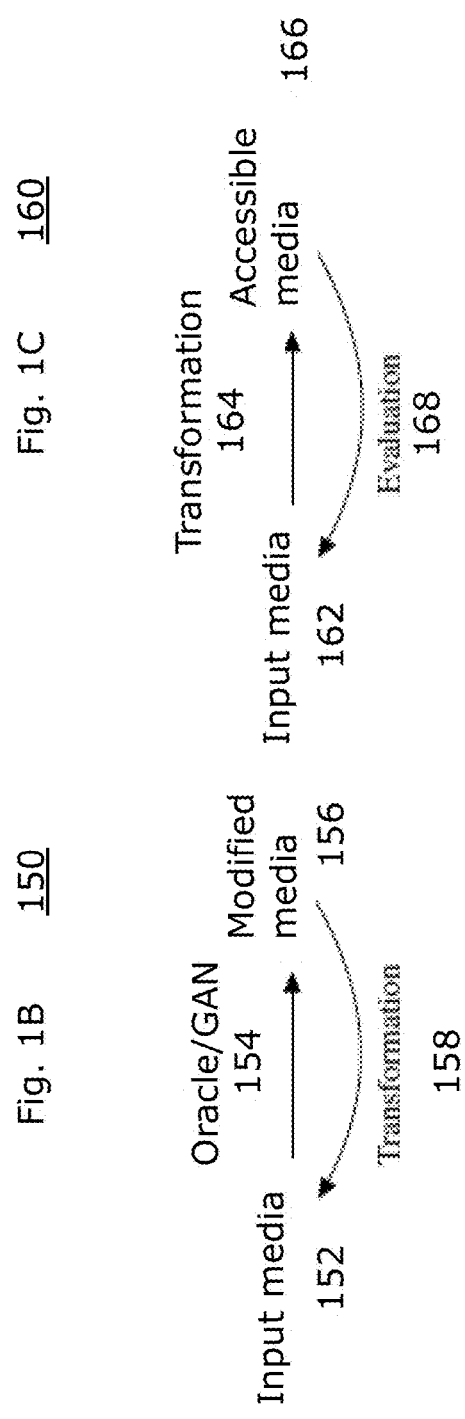

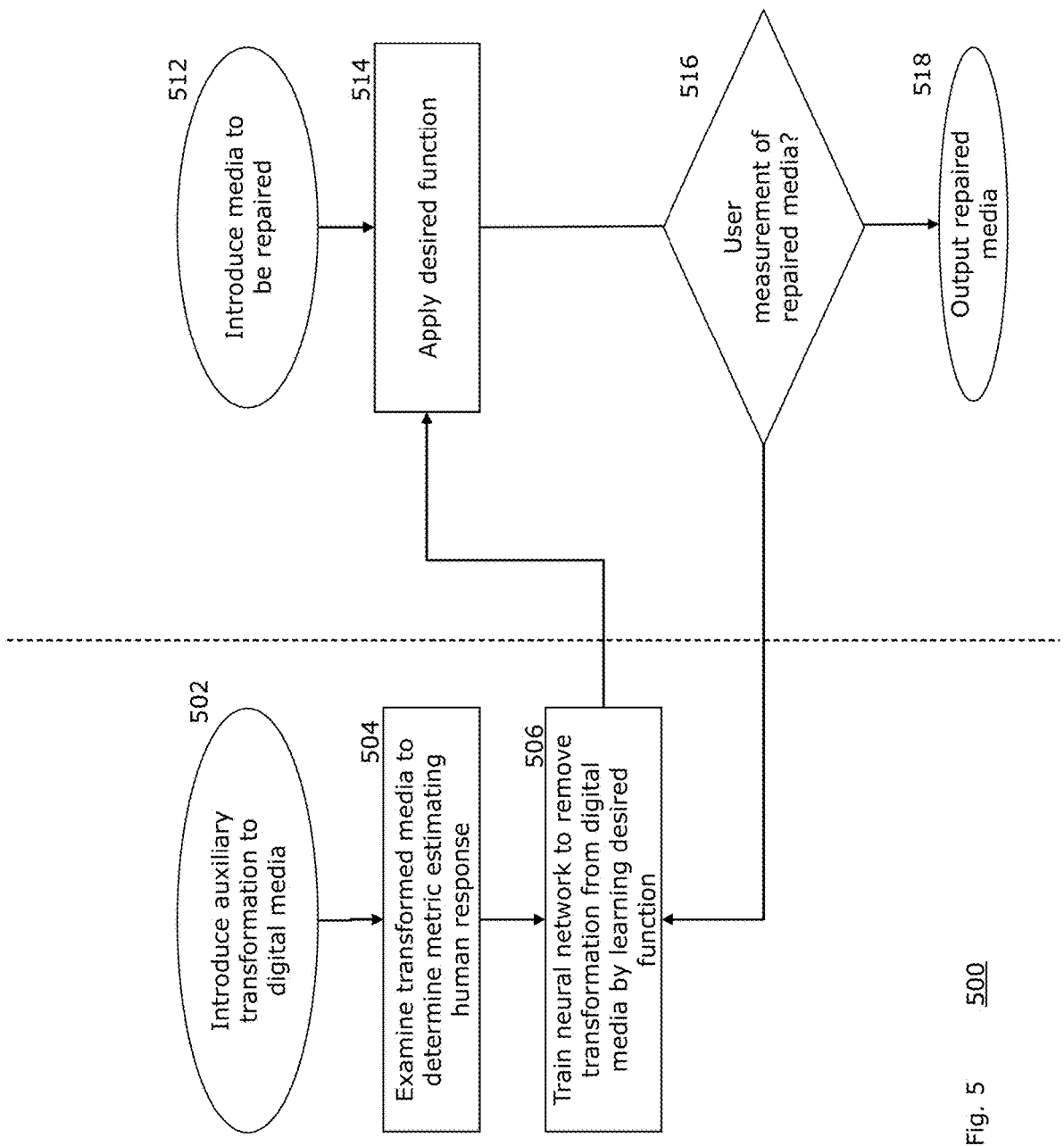
Fig. 5    500

COMPUTER METHOD AND APPARATUS MAKING SCREENS SAFE FOR THOSE WITH PHOTOSENSITIVITY

RELATED APPLICATION

This application claims the benefit of U.S. Provisional Application No. 62/698,652, filed on Jul. 16, 2018.

The entire teachings of the above application are incorporated herein by reference.

GOVERNMENT SUPPORT

This invention was made with Government support under Grant No. CCF-1231216 awarded by the National Science Foundation. The Government has certain rights in the invention.

BACKGROUND

Photosensitivity, an adverse reaction to light, or a visual stimulus such as a strobing light and rapidly-changing patterns, affects tens of millions of people worldwide. Approximately 0.5%-2% of the population (estimated at around 2 to 8 million Americans) suffer from some form of photosensitivity. Around 10% (or about 230,000) of those with epilepsy (estimated at 2.3 million in the US) are photosensitive. Photosensitivity may be associated with other disorders and it disproportionately affects children, for unknown reasons. Reactions range from seizures to migraines and discomfort.

Experiments on photosensitivity are difficult to conduct because exposure can heighten sensitivity to the adverse stimuli. Further, these reactions can come as a surprise because a significant fraction of those with photosensitive epilepsy discover their seizure disorder only when exposed to adverse stimuli. Reactions to adverse stimuli range from migraines to severe seizures which may result in permanent brain damage.

To protect those afflicted with photosensitivity, regulators in the UK and Japan have instituted TV broadcast standards to limit certain types of strobing although these address only a small subset of the stimuli that cause seizures or discomfort. To satisfy these requirements, engineers have designed filters for TV broadcasts to attenuate flashes, particularly red-blue flashes. However, other types of stimuli can cause adverse reactions, such as white-black flickers and rapidly-changing patterns. Further, white-black flickers and red-blue flashes have different ranges, flicker may occur differently, and certain patterns can be as disruptive as flickers or flashes. The differences between viewers are also stark, some are affected by a single bright flash, and the features of patterns or flashes that affect users are not well known although size in the field of view, frequency, color, the type of pattern are known to be involved. This is an acute problem as even recently major-release movies have triggered seizures.

SUMMARY

In an embodiment, a system and corresponding method, employing machine learning techniques, learns to detect problematic regions (e.g., regions with adverse stimuli) in media such as videos and learns to modify them, rendering them innocuous for those who are photosensitive. Applicant's method first automatically collects a large dataset of videos from the Internet and repositories therein, as a non-limiting example. Each video is then transformed by adding artifacts that may affect those with photosensitivity (e.g., adverse stimuli). For example, embodiments might insert a fast red-blue flicker in a region of a video, a medium-speed but larger white-black flicker, or a moving pattern that causes small repeated flashes. Each artifact is added at speeds and sizes quantified for each video as an estimate of the transformed video causing a human or animal response. Applicant notes that a person having ordinary skill in the art can recognize that discussions of human responses throughout this disclosure can also be applied to animal responses.

In an embodiment, a method includes, for each video of a repository of videos, duplicating the video of the repository and adding a respective artifact to the duplicated video. The method further includes training a machine learning model (e.g., neural network) to remove the respective artifact from the duplicated video based on differences of frames of each video of the repository to the duplicated video with the added respective artifact. The method further includes removing an artifact from an input video using the trained neural network, the input video being distinct from the videos of the repository of videos.

In an embodiment, the artifact can be an adverse visual stimulus. In an embodiment, the adverse visual stimuli can be a flash stimulus. In an embodiment, the neural network can be of the following: a residual bidirectional LSTM, a stacked LSTM U-Net, and a spatio-temporal autoencoder. A person having ordinary skill in the art can recognize that other neural networks or machine learning models can be used.

In an embodiment, duplicating the video and adding the respective artifact can be performed automatically by automatically generating random artifacts and inserting the randomly generated artifacts, as the respective artifacts, to the duplicated video. Automatically generating random artifacts further generates the artifacts randomly according to one or more user defined parameters.

Several applications can apply embodiments of this disclosure. In the consumer market, those with epilepsy (estimated at over 50 million worldwide) or other photosensitivity, can employ embodiments as a screen filter for computer monitors, TV monitors, smart devices, and the like. A screen or content filter can process content before it is displayed by a computer monitor, TV monitor, smart device, etc., and remove or attenuate artifacts such as flashes that cause epilepsy. A screen filter can protect those with epilepsy from accidental or intentional exposure. The screen filter can be tunable so that those with particularly high sensitivity can tune their filters to be more aggressive. In another embodiment, augmented reality glasses can be configured to filter artifacts/flashes causing epilepsy from screens in the user's field of view. In yet another embodiment, augmented reality glasses can transform text to be more readable for dyslexic users or transform faces to highlight facial features for users with autism spectrum disorder.

In the business market, embodiments of the filters could be built into browsers or employed by large content providers to ensure that all videos are safe for users that have photosensitivity. Since the prevalence of photosensitivity is almost ten times higher in children, embodiments of the present disclosure provide an advantage to video platforms by making them safe for children to view. In the longer term, given the wide impact and low cost of applicant's approach, regulators and content distributors could adopt embodiments of the present disclosure to protect everyone in society.

In an embodiment, a method, and corresponding system and non-transitory computer readable medium storing instructions configured to cause a processor to execute steps are configured to introduce an auxiliary transformation to a digital media, resulting in a transformed digital media by generating the auxiliary transformation with a transform function. The method is further configured to evaluate the transformed digital media to generate a metric estimating a human response to the transformed digital media altered by the introduced auxiliary transformation. The method is further configured to train a neural network to remove the auxiliary transformation from any digital media by learning a desired transformation function from the transformed digital media and the metric associated with the transformed digital media.

In an embodiment, the desired transformation function is an inverse function of the auxiliary transformation.

In an embodiment, introducing the auxiliary transformation further includes introducing a respective auxiliary transformation to each digital media of a collection of original digital media, resulting in a collection of transformed digital media by generating the auxiliary transformation with the auxiliary transform function.

In an embodiment, the auxiliary transform function is specified by a designer.

In an embodiment, the auxiliary transform function is learned by a second neural network.

In an embodiment, generating the metric estimating the human response to the transformed digital media includes employing a predefined function to estimate the human response based on the transformed media.

In an embodiment, generating the metric estimating the human response to the transformed digital media includes collecting physiological measurements or behavioral measurements from one or more testing users experiencing the transformed digital media.

In an embodiment, generating the metric estimating the human response to the transformed digital media includes employing a second neural network that is trained as a proxy for a human physiological measurement or behavioral measurement.

In an embodiment, the media type of the collection of digital media includes videos, images, audio, text, virtual or augmented reality scenes, three-dimensional (3D) video, or 3D scenes.

In an embodiment, the auxiliary transformation includes
  a) introduction of flashing,
  b) a modification of features representing emotions in an image, video, or augmented reality experience,
  c) a highlighting of features representing emotions in an image or video, or
  d) an obscuring of features that are irrelevant to emotions in an image or video,
  e) highlighting or obscuring features in the media representing a distraction,
  f) highlighting a key out of a sequence of actions,
  g) highlighting future behaviors for the user or other agents,
  h) highlighting features indicating social interactions,
  i) a modification of text,
  j) human annotations, or
  k) modification of audio features.

In an embodiment, the method further includes repairing a given media to a modified media by applying the desired function to the given media. The modified media is generated by application of the desired function to cause a human response estimated by a metric having a particular value.

In an embodiment, the method further includes adjusting the neural network based on further behavioral measurements or physiological measurements from a user experiencing the modified media.

In an embodiment, the machine learning model is a neural network.

In an embodiment, the digital media can include media that was never transformed by the auxiliary function.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 1B is a flow diagram illustrating a schematic embodiment of Applicant's system and method.

FIG. 1C is a flow diagram illustrating a schematic embodiment of Applicant's system and method after the training of FIG. 1B.

FIG. 5 is a flow diagram illustrating a process employed by an embodiment of Applicant's present disclosure.

DETAILED DESCRIPTION

A description of example embodiments follows.

Applicant presents methods and systems that transform unsuitable (or less suitable) media to suitable media for viewers with automatic photo or video editing. In an embodiment, a method and system automatically learns media filters with respect to patterns, frequencies, and sizes, for example within a field of view of a frame or multiple frames of a video. Applicant discloses embodiments for training transformations of media (e.g., media transformations including at least video-to-video, image-to-image, audio-to-audio, etc.). Applicant describes an embodiment using video transformation throughout, but a person having ordinary skill in the art can recognize that any type of media (e.g., video, audio, still picture, animation, multimedia, etc.) can be substituted.

A person having ordinary skill in the art can recognize that the transformation that results from each system can vary based on the respective media that is input during training.

Figure 1A:
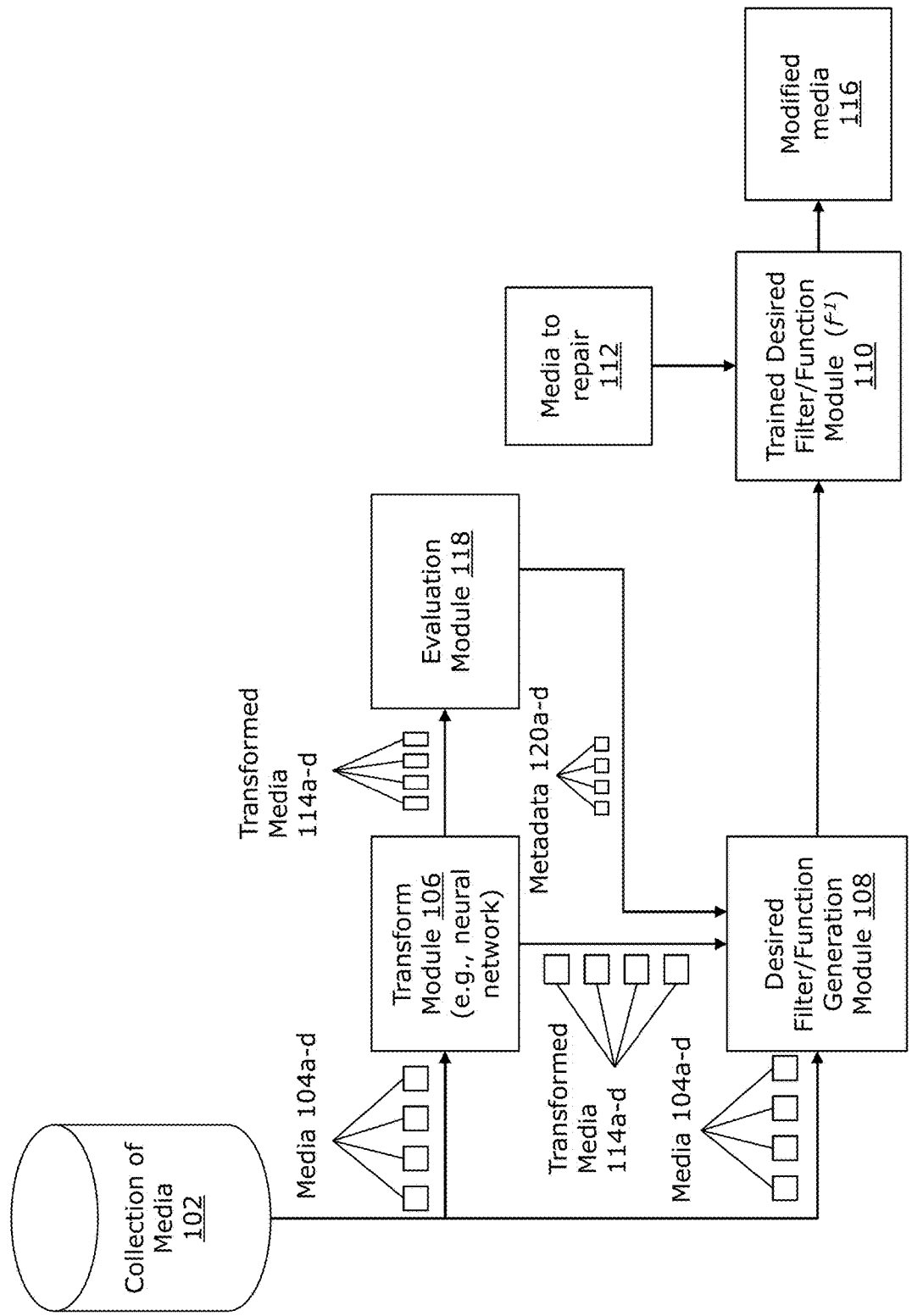
FIG. 1A is a schematic diagram illustrating an example embodiment of the present disclosure.
Figure 2:
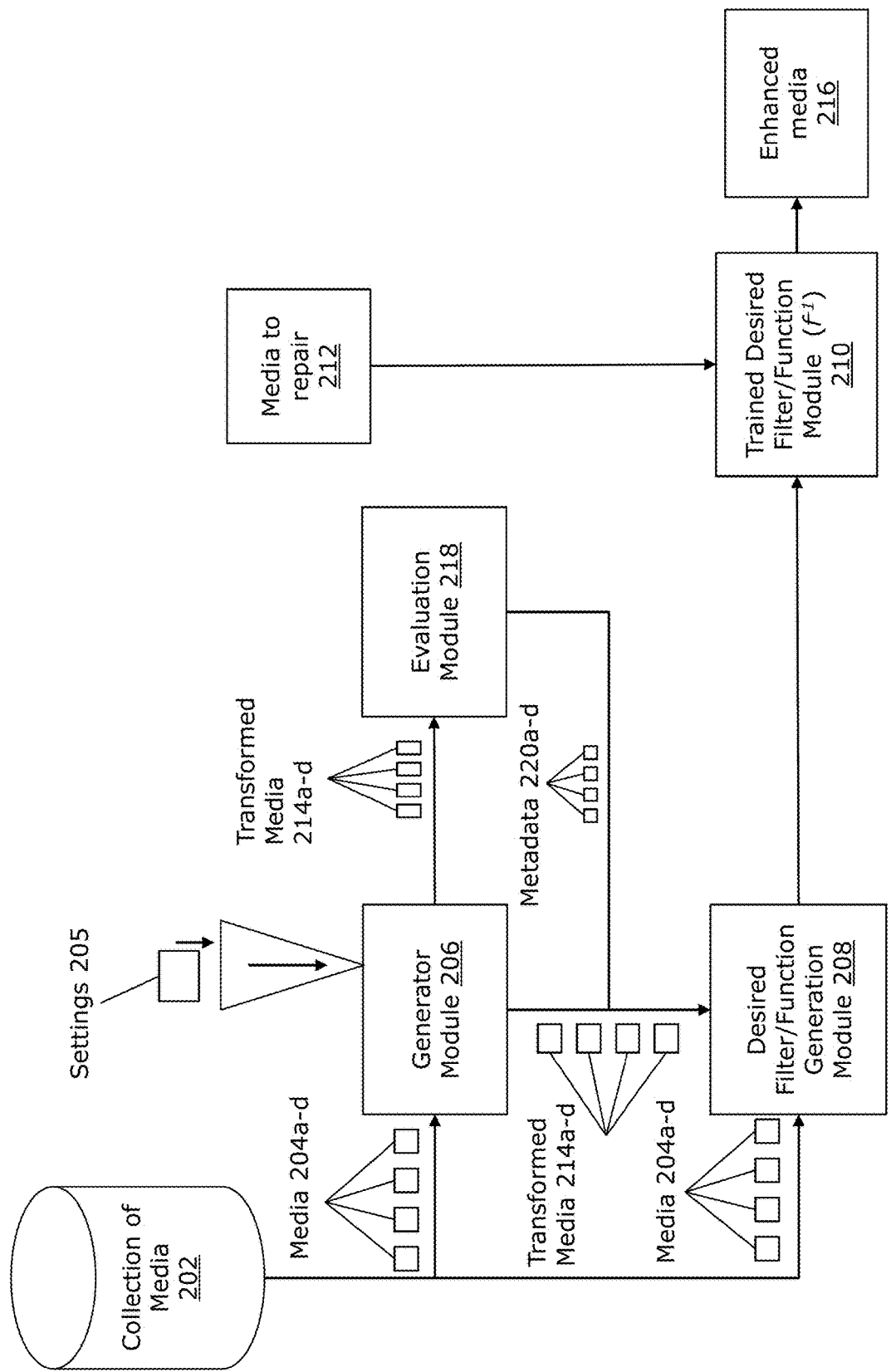
FIG. 2 is a schematic diagram illustrating an example embodiment of the present disclosure employing a generator function/module.

In a first embodiment, such as the system illustrated in FIGS. 1A-2, a generator module/function (e.g., an oracle) inserts one or more adverse stimulus (e.g., harmful) into existing media, such as videos, and then the system trains a neural network to remove the inserted adverse stimulus from the media to return the media to its original state. In a second embodiment, such as the system illustrated in FIGS. 1A-1C and 3, a neural network (e.g., a generative adversarial network (GAN)) and detector module learns to insert adverse stimuli, and then the system trains a neural network to learn the desired (e.g., inverse) function as well. In a third embodiment, such as the system illustrated in FIGS. 1A-C and 4, a model for the human visual system (e.g., physiological feedback from a human user viewing the media) can predict which stimuli are adverse, and the system trains a desired function based on the human feedback. In each embodiment, a system transforms a video with adverse stimulus into a video without such adverse stimulus. A person having ordinary skill in the art can recognize that in other embodiments, as disclosed further below, the adverse stimuli can be other transformations, like highlighting or dimming particular areas of an image or video. A person having ordinary skill in the art can recognize that other transformations can be employed as appropriate with other applications.

In the first and second embodiments, each neural network is trained on videos taken from the Internet or a video repository therein that are likely not to have adverse stimulus. These embodiments first modify/augment the videos to include adverse stimulus. Then, the system trains a neural network to recover the original, unmodified videos from an input of the augmented videos paired with the original videos, as well as metadata regarding the extent of modification of the augmented videos.

In the third embodiment, a neural network receives adverse stimuli and learns to transform them into stimuli that the model for the visual system considers acceptable based on physiological or behavioral measurements from a human user.

In each embodiment, however, the neural networks are not specific to a type of transformation, as the goal of the network is to be agnostic about how to perform the transformation. As a result, a video-to-video network is not tuned in any way to reduce a specific type of artifact (e.g., flash mitigation or photosensitive epilepsy). By leaving each network agnostic to a specific type of transformation, training the networks with different data sets and/or added artifacts can lead to novel kinds of transformations that can help with other accessibility issues. For example, the networks can be trained to perform other video transformations. The networks can also be trained to transform other media, such as images (e.g., emotion amplification, etc.) or audio.

In an embodiment, a filter embodying the principles (model, neural networks, approach, etc.) of the present invention is shown and described. In a first embodiment, a collection (e.g., above a trainable threshold) of videos are downloaded from the Internet or another video repository. The videos can be selected randomly. A transform module adds adverse (e.g., harmful) stimuli into these videos. For example, in an embodiment training a model for face recognition, the transform module can add in faces with hard-to-read emotions at different resolutions, as a non-limiting example. In the example of photosensitive epilepsy, the module adds in flashes in different color spaces and several kinds of patterns of different sizes at different frequencies, as is described in more detail below. Some videos are modified to an extent that they are above the threshold (e.g., high luminance flashes between 3 Hz-49 Hz) at which they may cause seizures. Other videos are modified but to a smaller degree such that they are below the threshold at which they trigger seizures. The resulting modified corpus contains modified videos, both positive and negative examples, paired with original videos.

Respective neural networks train on such media/video pairs (e.g., modified video and original video pairs) and learn to reverse the auxiliary transformation that was applied to the modified video with respect to the paired videos. Undoing the transformation trains the network to remove artifacts like those introduced by the auxiliary transformation in all videos, even those which were never transformed in the first place. Learning to remove flashes that are added in allows you to remove flashes from any video. With sufficient data (e.g., 10,000-100,000 or more examples), a video-to-video network learns to make any media safe that has the properties introduced by the auxiliary transformation(s). A safe (e.g., free of adverse stimuli ill-effect) video that maintains a quality level of the original video is output as a result.

In particular, in one embodiment the disclosure employs three types of networks which can learn video-to-video transformations: a bidirectional convolutional long short-term memory (LSTM) that learns embeddings of the video and then decodes a modified video (see, e.g., Baccouche et al., 2010), a novel architecture that combines a U-net with a bidirectional stacked LSTM (Ronneberger et al., 2015), and an adapted spatio-temporal autoencoder (Patraucean et al., 2015). In a forward/synthesis pass, the neural networks automatically create a corpus or dataset that includes pairs of videos, each pair having (i) an original, untransformed video, and (ii) a video that is transformed to hide or highlight some feature. After creating the corpus, the neural networks, in an inverse pass, learn a new video-to-video mapping as disclosed below.

The inverse pass transforms unsafe videos (e.g., videos with adverse stimuli) into safe videos (e.g., videos without the adverse stimuli) without (a) losing video quality and (b) compromising videos when no unsafe (e.g., adverse) stimuli are present. Applicant illustrates three neural networks for processing the corpus of videos paired with problematic videos.

The residual bidirectional LSTM demonstrates how well such methods work even with few parameters. Long short-term memory (LSTM) (Hochreiter and Schmidhuber, 1997) networks are recurrent neural networks that integrate reasoning across time with a gated memory unit. Input videos are processed frame-by-frame by a convolutional neural network (CNN) with 4×4 convolutions having just four filters, followed by batch normalization and rectified linear unit (ReLU or RELU) activation. A bidirectional convolutional LSTM (Xingjian et al., 2015) takes as input this embedding for each frame of a video, updates its internal state, and predicts a new frame feature vector. Bidirectional LSTMs can integrate information from both the future and the past, potentially allowing them to more accurately detect stimuli such as flashes and changing patterns. In this case, to predict an image, a final layer includes a 3×3 convolution with three filters, one filter for each color channel (e.g., Red, Green, and Blue (RGB)), the output of which are added to the original image to produce the result. Residuals have been shown to be far easier to learn because the network learns and represents only the difference between the input and the desired output rather than needing to embed the entire high-dimensional input. The residual bidirectional LSTMs work well when a human-designed oracle introduces flashes but have difficulty adapting to the more complex forms of flashing and patterns produced by the GAN.

Figure 6:
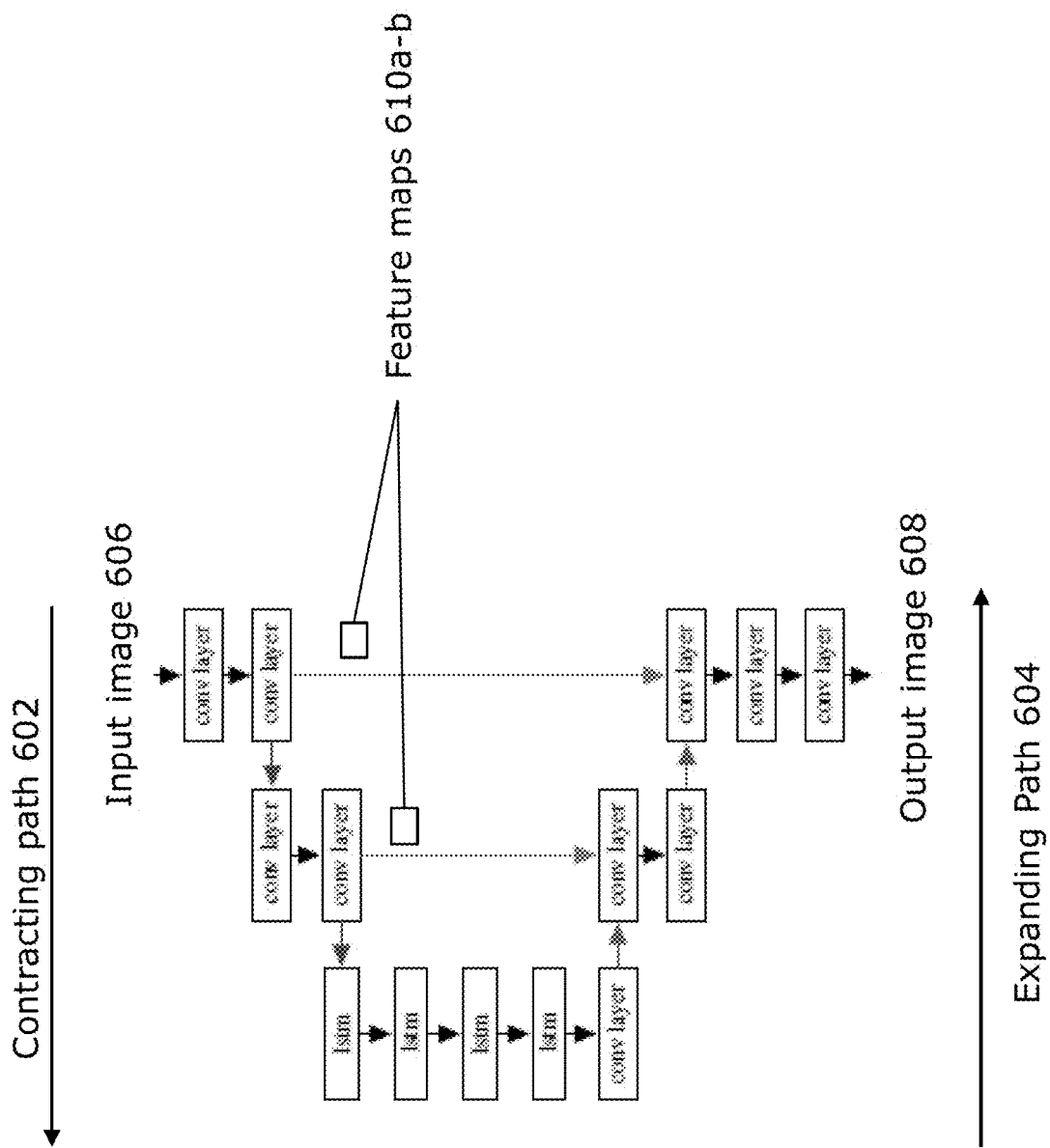
FIG. 6 is a diagram illustrating an example embodiment of a long short-term memory (LSTM) U-Net architecture.

Next, Applicant adapts the U-Net architecture (Ronneberger et al., 2015) to video-to-video transformations, which is described in further detail in relation to FIG. 6. U-Net is an approach to image segmentation that finds low-dimensional embeddings for an input image and then decodes those embeddings into a segmentation of the image. The U-Net consists of two paths: (1) a contracting path that lowers the dimensionality of the input and (2) an expanding path that raises it. The outputs of the contracting path are forwarded to the expanding path at each step but doing so for each internal step instead of simply at the input and output layers. In embodiments, the contracting path and expanding path include numbers of convolutional and pooling layers. In embodiments, the network consists of 4 layers of 3×3 convolutions. Rather than predicting a segmentation map, Applicant's disclosure predicts an RGB (red-green-blue) image per frame. Embodiments stack four bidirectional convolutional LSTMs, one per U-Net layer, with 64 filters in the first and last layers and 32 in the final layer, to process the embedded data in this architecture allowing information to flow across frames of the video when reconstructing the input. This network is significantly larger than the previous one described and is better designed to progressively eliminate undesired portions of the input or enhance the input through multiple processing stages. Having access to the temporal structure of the video is advantageous, as a per-frame U-Net cannot learn to perform the required transformations. Applicant's disclosure is the first application of a stacked LSTM U-Net to video-to-video transformations.

The third architecture adapts a method which learns to compute optical flow in videos. Spatio-temporal autoencoders (Patraucean et al., 2015) (STA), take each frame as input and predict an output frame based on the sequence of frames observed up to that point. Unlike the previous networks, SPAs are neither bidirectional nor do they predict a residual. They embed the input into a low-dimensional space, in the present disclosure using a 4-layer 32-filter 3×3 convolutional network with ReLU activation. This embedding is used by two stacked convolutional LSTMs with 32 filters to predict the optical flow. The network then reconstructs its beliefs about the next frame of the video by combining the embedding of the current frame with its predicted optical flow and decoding that prediction using the inverse of the embedding network. Applicant adapts this approach to flash mitigation. Intuitively, to compute optical flow, Applicant's disclosure predicts the next frame based on previous frames, or in an embodiment, predicts future behavior of a flashing stimulus or pattern to determine if one should suppress it.

FIG. 1A is a schematic diagram illustrating an example computer-implemented embodiment 100 of the present disclosure. A transform module 106, which can be implemented as a neural network in an embodiment, receives media 104a-d from a collection of media 102, such as a public video repository like YouTube®. A person having ordinary skill in the art can recognize that media 104a-d can be a large number of media. For example, in a non-limiting embodiment, the media 104a-d can be 10,000 or more videos. The transform module 106 transforms the received media 104a-d by adding in an artifact, such as adverse stimuli, resulting in transformed media 114a-d. The adverse stimuli, in one embodiment, can be flash effects that are known to cause seizures. However, the media can be transformed in other ways. For example, in an embodiment where the media are pictures of faces, the transformation can be to change emotion of those faces, to add in faces with a particular emotion, or to highlight emotive aspects of a face or de-emphasize unemotive aspects of a face (e.g., by highlighting or dimming).

An evaluation module 118 is configured to receive transformed media 114a-d and generate metrics represented by metadata 120a-d that estimate a human response to the transformed digital media altered by the introduced transformation. For example, the evaluation module can estimate a human response to added flashes into a video, and the resulting metric can indicate a likelihood of a seizure being caused by such a video.

A desired filter/function generation module 108 receives the original media 104a-d and the transformed media 114a-d, and learns a desired filter/function (e.g., an inverse function). The desired filter/function generation module 108 pairs each transformed media 114a-d with its original media 104a-d and metadata 120a-d and determines transform to restore each transformed media 114a-d to its corresponding original media 104a-d. When the number of media is large, the desired function that results, trained desired filter/function module 110, can be effective at transforming other media to remove introduced artifacts.

Once the desired filter/function generation module 108 is fully trained, the method and system 100 can use the desired filter/function to repair videos. The trained desired filter/function module ($f^1$) 110 can receive the media to be repaired 112, apply the function $f^1$, and output a repaired media 116 (e.g., as a file or on a display).

FIG. 1A is a diagram illustrating a schematic embodiment 100 of Applicant's system and method. However, FIGS. 2-4B are block diagrams 200, 300, and 400, respectively, illustrating other embodiments of Applicant's system and method.

FIG. 1B is a flow diagram illustrating a schematic embodiment 150 of Applicant's system and method. An input media 152 is converted into a modified media 156 by an Oracle/GAN 154. As is described herein, the input media 152 can be one of a collection of input media. Such a modification can be inserting adverse stimuli into a video, or highlighting a facial feature. After modification, a neural network can be trained to apply a transformation 158 that reverses the transformation applied by the Oracle/GAN 154 for any media.

FIG. 1C is a flow diagram illustrating a schematic embodiment 160 of Applicant's system and method after the training of FIG. 1B. An input media 162 is transformed 164 to an accessible media 166 using the method and corresponding systems (e.g., neural networks) described in relation to FIG. 1B, for example. In addition to applying the neural network generated transformation trained in FIG. 1B, however, FIG. 1C demonstrates that using the system after initial training can continue to train the neural network based on physiological or behavioral feedback. A person having ordinary skill in the art can recognize that physiological measurements or behavioral measurements can include measurements from a sensor or imaging system, response from a human (e.g., survey or ranking response), or other feedback.

FIG. 2 is a schematic diagram illustrating an example computer-implemented embodiment 200 of the present disclosure employing a generator function/module 206. FIG. 2 illustrates a generator module 206 that receives media 204a-d from a collection of media 202. The generator module 206 introduces artifacts to the media 204a-d to produce transformed media 214a-d according to settings 205, which indicate the type of artifact to introduce (e.g., the range of magnitude of the artifact). An evaluation module 218 evaluates the transformed media 214a-d and generates metadata 220a-d representing a human response to the transformed digital media altered by the introduced transformation.

Each respective media 204a-d is paired with the transformed media 214a-d that the generator module 206 added artifacts to as well as the metadata 220a-d. The pair of media 204a-d and 214a-d are also associated with respective metadata 220a-d, which represents an estimate of a human response to the transformed media. Using videos as an example media, the system 200 gathers a collection of videos 202 that have a low likelihood of having an artifact (e.g., from YouTube, etc.). In an embodiment, the videos are processed in fixed size chunks. For example, for a given video, the system can optionally break the video down into tiles, such as 200×200 pixel regions of 100 frames each from the video segment, and then process each chunk in sequence. However, a person having ordinary skill in the art can recognize that videos with various sizes, various lengths, or streaming video can also be used.

The generator module 206 receives a video (V) (e.g., media 204) and produces a corrupted video ($V^1$) (e.g., transformed media 214). The generator module's 206 function can be denoted as $g(V)=V^1$, where $V^1$ is a version of V having artifacts introduced to a particular degree, represented for each transformed media 214a-d by the metadata 220a-d, with subscript theta denoting the parameters of a network. In other words, media 204a-d represents V while transformed media represents $V^1$. A person having ordinary skill in the art can recognize that the generator module 206 not only produces corrupted videos, but videos that are corrupted to a degree indicated by the metadata 220a-d. For example, in the flash example, the level of corruption that affects particular humans may vary. By recording metadata 220a-d for each transformed media 214a-d, the network can learn to remove flashes for varying level of flashes as desired by the user after training.

The generator module 206 further produces a distribution (e.g., bimodal Gaussian) of corruption as specified by the limits of the settings 205 (e.g., configurable degree). The evaluation module 220 further provides metadata 220a-d representing estimates of the human response to the media. In another embodiment, the metadata 220a-d can also be a binary value (e.g., whether the artifact introduced is above a threshold).

After introducing corruption to the video, a neural network of the desired filter/function generation module 208 learns a desired function (e.g., inverse function) to transform transformed media 214a-d back to media 204a-d as indicated by the metadata 220a-d. For example, the desired filter/function generation module 208 learns to transform for varying levels of transforms. For example, the desired filter/function can remove artifacts having a metric level $\chi$ or lower, for any $\chi$ introduced by any user. Alternatively, the desired filter/function can remove artifacts having a metric level $\chi$ or higher for any x.

In one example, a neural network can perform such learning by decreasing the size of each frame of the video progressively until a certain point, and then progressively make the video larger again, while using information from previous larger versions to restore the quality. The neural network receives the transformed media 214a-d and tries to make the output as similar as possible to the original media 204a-d.

As an expression, the generator module's 206 output can be expressed as:

Gen(V→(V', Threshold), where V' is the transformed media, and Threshold is an indication of whether the transformation is above or below the threshold introduced by the user.

As an expression, generative module can either be specified by a designer or learned using an objective function which modifies videos while attempting to make distinguishing videos which are above and below threshold as difficult as possible. This is accomplished by using a GAN-style architecture which simultaneously learns the transformation and the discriminator.

Once the desired filter/function generation module 208 is trained, the method and system 200 can use the desired filter/function 210 to repair videos. The trained desired filter/function module ($f^1$) 210 can receive the media 212 to be repaired, apply the function $f^1$, and output a repaired media 216 (e.g., as a file or on a display).

Figure 3:
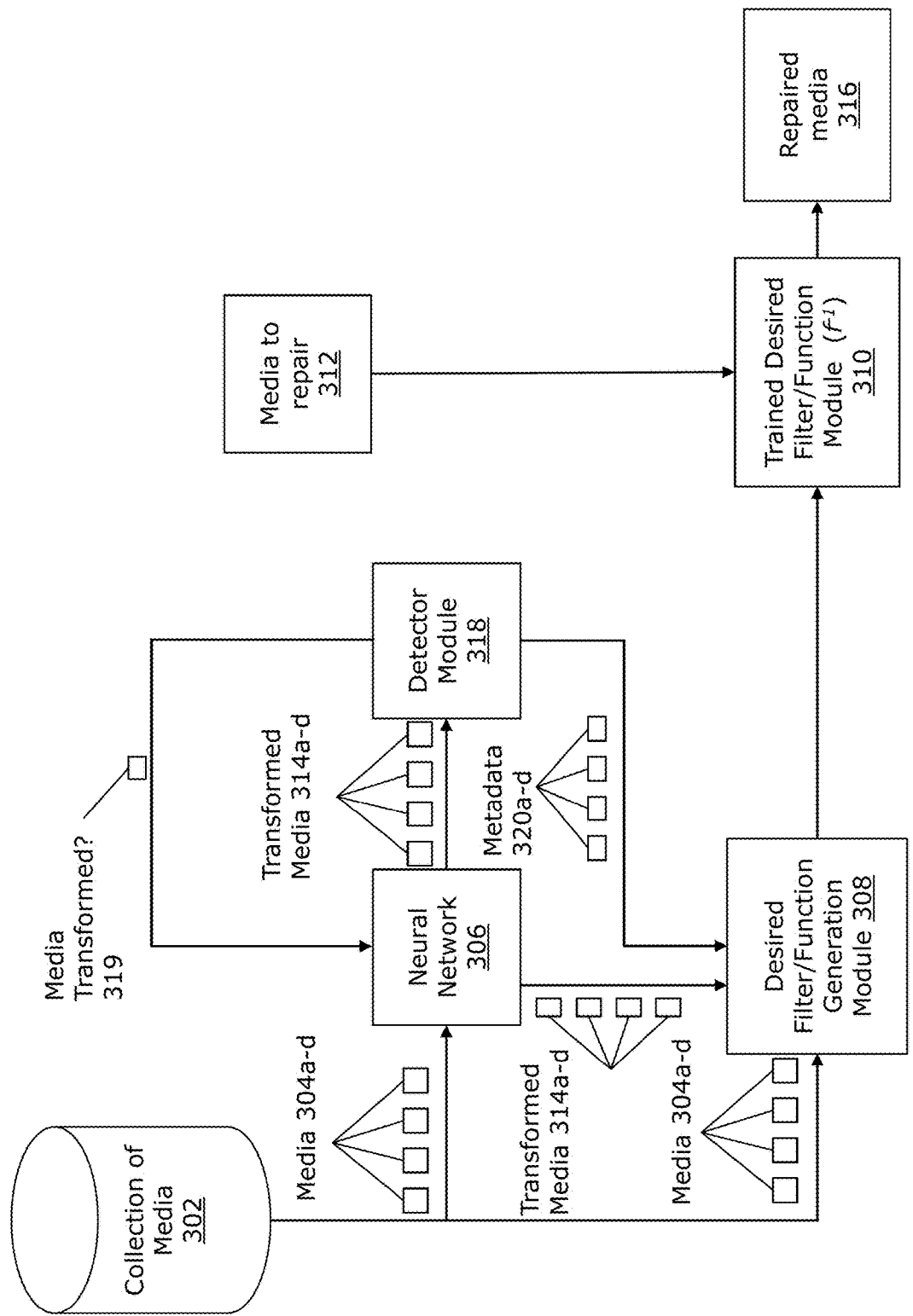
FIG. 3 is a schematic diagram illustrating an example embodiment of the present disclosure employing a neural network paired with a detector module.

FIG. 3 is a schematic diagram illustrating an example embodiment 300 of the present disclosure employing a neural network paired with a detector module 318. A first neural network 306 (e.g., generation network 206) learns how to generate the transformation ($\theta_G$) and a second neural network ($\theta_T$) of the desired filter/function generation module 308 learns a desired function 310 after the transformation is applied. To assist the generation network ($\theta_G$) 206, a detector module 318 generates an output indicating whether a given video has a certain artifact (e.g., an observed estimated human response above a detectable level). The detector module 318 can be denoted as Det(Gen$_\theta$(V)), and generates an output approaching/at one end of a scale for not detecting the artifact (e.g., 0) and approaching/at the other end of the scale for detecting the artifact (e.g., 1). A person of ordinary skill in the art can recognize that while an exemplary 0-to-1 scale is disclosed, other scales can be employed. The generator network ($\theta_G$) outputs a video that, when evaluated, is at a diverse set of points on this scale of the Det(Gen$_\theta$(V)) function. In an embodiment, the detector module 318 provides media transformed feedback 319 to the neural network 306. The neural network can use the feedback, for example, to ensure that the transformed media 314a-d is encouraged to be at either end of the scale for detecting the artifact until the neural network 306 adequately applies a transform according to the detector module 306. The transformation network ($\theta_T$) (e.g., inverse filter/function generation module 308) learns to convert the transformed media 314a-d to the original media 304a-d for media having metadata/a detection module 318 output metadata 320a-d close to 1, and learns to leave transformed media 314a-d having a detection module 318 output metadata 320a-d close to 0 alone.

As described above, the output of the detection module 320 can be expressed as:

Det(Gen$_{\theta_T}$(V)), where its output is driven to 0 or 1, or another scale as chosen by a designer (e.g., −1 to 1, etc.).

When the detection function is driven to 0, the neural network 306 can learn the output of the transformed media 314a-d or the neural network 306 can attempt to generate a new transformed media 314a-d until one with an adverse stimulus is created.

Once the desired filter/function generation module 308 is fully trained, the method and system 300 can use the desired filter/function 310 to repair videos. The trained desired filter/function module ($f^1$) 310 can receive the media 312 to be repaired, apply the function $f^1$, and output a repaired media 316 (e.g., as a file or on a display).

Figure 4A:
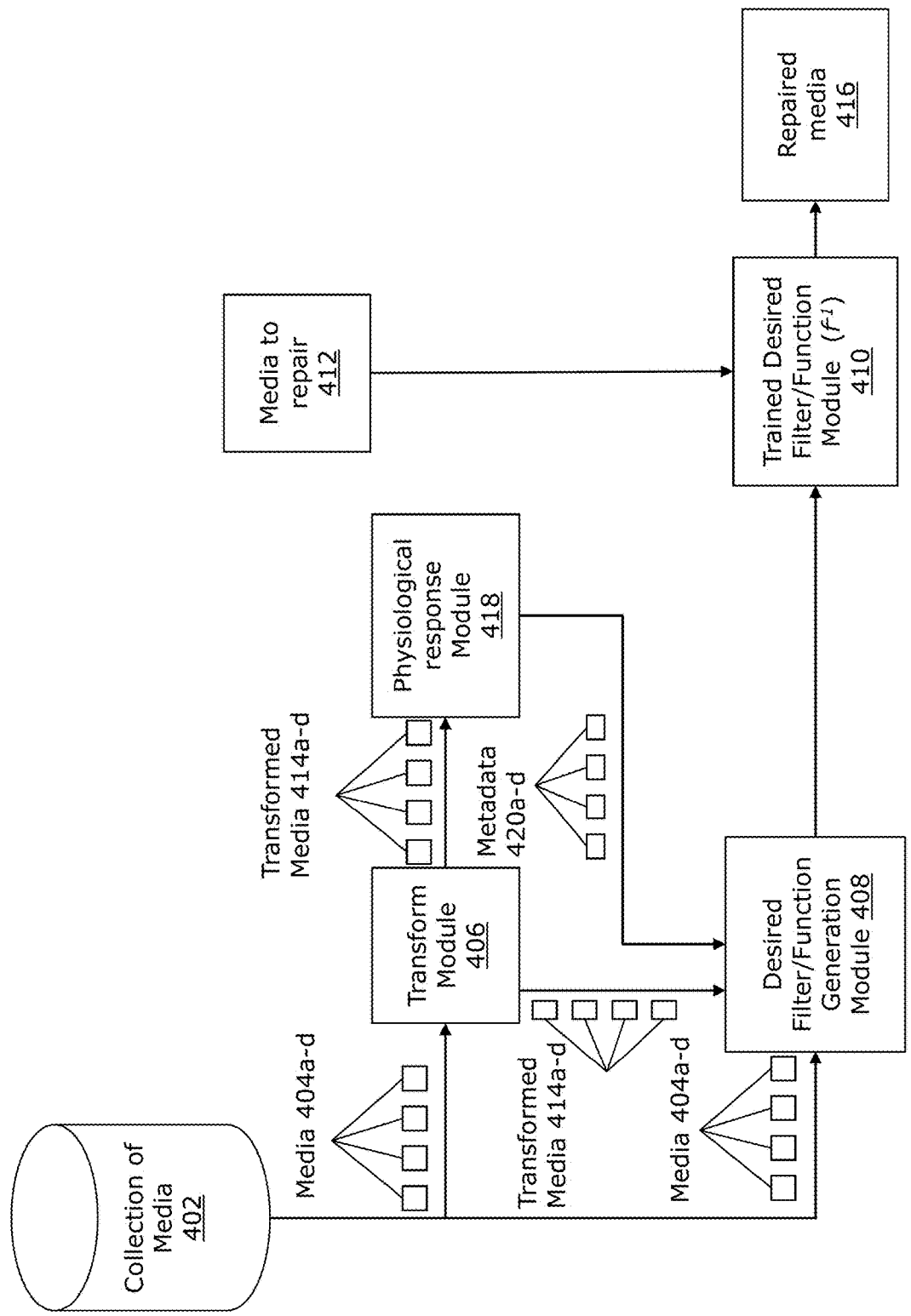
FIG. 4A is a schematic diagram illustrating an example embodiment of the present disclosure employing a physiological measurement module.

FIG. 4A is a schematic diagram illustrating an example computer implemented embodiment 400 of the present disclosure employing a physiological measurement module.

A physiological response module 418 employing a test such as a human electroencephalogram (EEG) or another physiological or behavioral measurement can be employed. A collection of media 402 are can be known either to be good or have a problem, or that characteristic can be discovered during the process. In embodiments, artifacts can be generated by a transform module 406 or a neural network therein as described above, or provided by other means. The transformed media 414a-d is shown to a human that is being observed by a physiological measurement module 418 administering an observable physiological measurement, such as an EEG, eye-tracking, functional Magnetic Resonance Imaging (fMRI), Magnetoencephalography (MEG) scan, or voice recording (e.g., for dyslexia applications), or a behavioral measurement such as a survey, yes/no question, rating scale, accuracy or time spent while performing a task, etc. The physiological measurement module 418 can capture physiological measurements or behavioral measurements (e.g., responses, survey responses, etc.) from the human viewing the transformed media 414a-d to determine whether the media has an artifact. For example, in media having flashing, the output of the physiological measurement module 420 may indicate if the human is experiencing markers of a seizure or pre-seizure. In another example, in media that is testing for ease of reading of dyslexia, a human simply reading back text can indicate whether the word was read correctly or incorrectly, or which words or letters in particular the user got correct or incorrect. These test results serve as the metadata 420 that is associated with each transformed media 414a-d respectively. The physiological or behavioral measurement can be converted/normalized to a 0-to-1 scale (e.g., where 0 indicates the media is free of artifacts and 1 indicates the media has artifacts), and that value is used by the neural network as an argument to identify videos with an artifact.

Once the desired filter/function generation module 408 is fully trained, the method and system 400 can use the desired filter/function 410 to repair videos. The trained desired filter/function module ($f^1$) 410 can receive the media 412 to be repaired, apply the function $f^1$, and output a repaired media 416 (e.g., as a file or on a display).

Figure 4B:
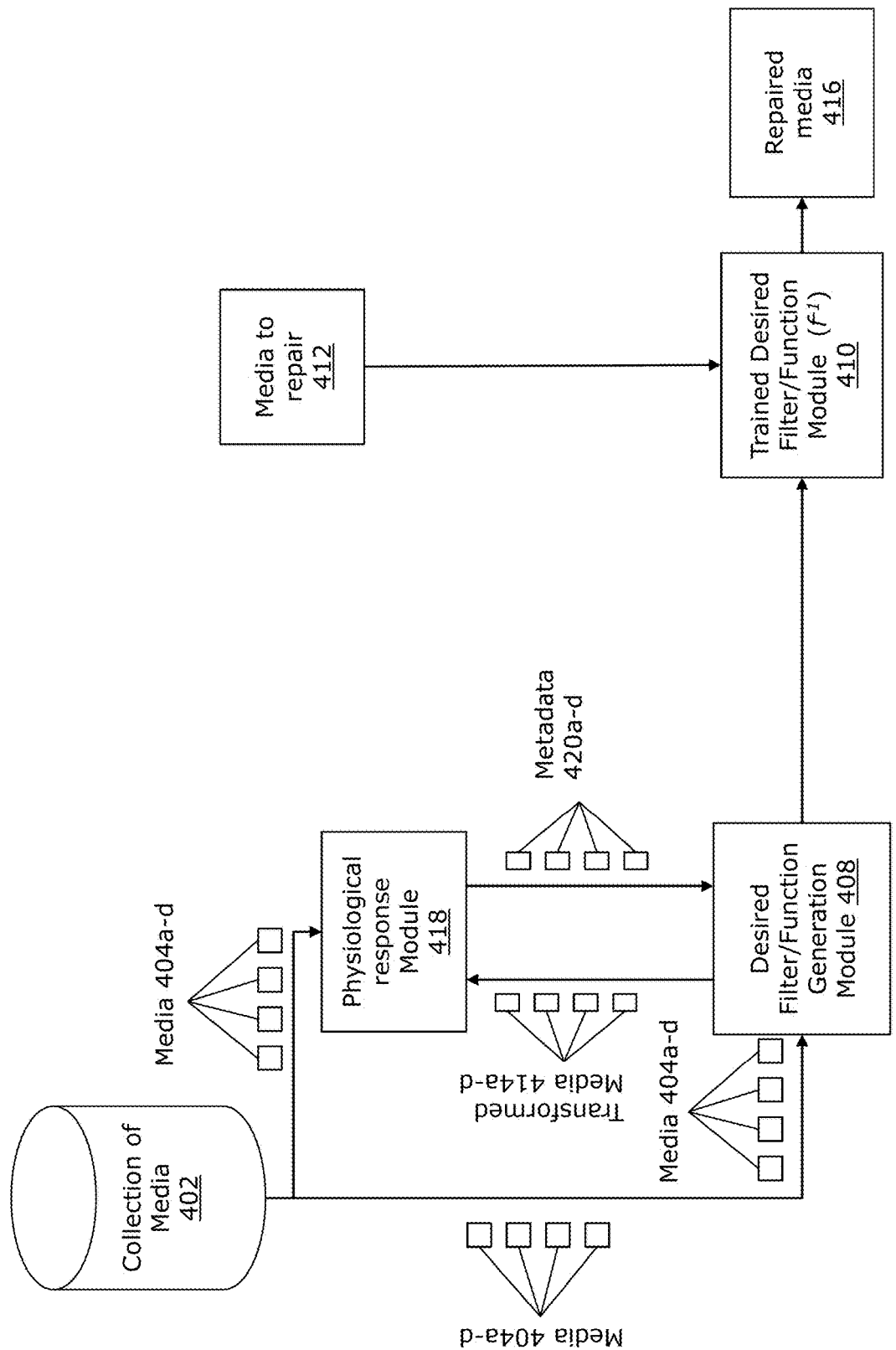
FIG. 4B is a schematic diagram illustrating another embodiment of Applicant's system employing a physiological measurement module.

FIG. 4B is a schematic diagram illustrating another embodiment 450 of Applicant's system. In this embodiment, some of the collection of media 402 are known to have adverse stimuli. The media 404a-d is sent both to a physiological measurement module 418 and a desired filter/function generation module. The desired filter/function generation module 408 then receives metadata from the physiological measurement module 418 that indicates which of the media 404a-d includes adverse stimuli. The desired filter/function generation module 408 can modify the media 404a-d into transformed media 414a-d until the physiological measurement module 420 provides metadata 420 indicating the adverse stimuli is removed.

In addition to flash suppression, Applicant's method can be applied to other artifacts introduced to media. For example, for learning disabilities such as dyslexia, Applicant's method can be applied to learn contrast enhancement or magnification of text in images or video to help such a user with reading the text. In another embodiment, emotions in an image or video can be learned, using Applicant's method, to be amplified for users who have difficulty perceiving them or suppressed for users who are distressed by them.

In other embodiments, the method can be applied to audio files. For example, like in video, audio also contains indications about the emotional state of the speaker. Applicant's method and system can learn to enhance or diminish such information from an audio file.

In other embodiments, the system and method can be applied to amplify colors or contrast in images or videos for people who are color blind or people with low visual acuity.

Further, a person having ordinary skill in the art can recognize that in Applicant's method, dimensions of media that cannot be easily described by humans can be detected as stimuli (either adverse or beneficial) and amplified or reduced by Applicant's system. For example, when amplifying emotions in a person's face, studies have found that certain facial features, such as eyebrow movement, are particularly indicative of human emotion. Other similar knowledge may exist. However, with Applicant's system and method, other aspects of a human face that have been previously undiscovered or are hard for humans to quantify can be discovered as more indicative of human emotion, and therefore can be amplified by Applicant's system. This phenomenon can be applied to any of the other applications described herein as well.

FIG. 5 is a flow diagram illustrating a computer-based process 500 employed by an embodiment of Applicant's present disclosure. A person having ordinary skill in the art can recognize that process elements 502, 504, 506 are part of a training process, and elements 512, 514, 516, and 518 are part of an implementation process after an initial training is complete.

To train, the process 500 begins by introducing an auxiliary transformation 502 to digital media as illustrated and described above in FIGS. 1-4. The process can evaluate 504 the transformed media to determine a metric that estimates a human response to the transformed media (e.g., whether the transformation causes a physiological or behavioral response in the human). Then, based on that evaluation 504, the method trains a neural network to learn 506 a desired function (e.g., remove the introduced transformation) on digital media. For example, the network learns to transform media having transformation of different levels of metrics, thereby allowing removal of artifacts causing physiological and/or behavioral responses in humans having different levels of sensitivity.

On the implementation side, media to be repaired is introduced (512). The desired function, learned in element 506, is applied 514 to the media to be repaired. Optionally, the desired function receives an input metric indicating which level of response an artifact causes to remove or change. A user measurement/response (e.g., physiological or biological response) 516 can further train the neural network 506 if entered. Then, the repaired media is output 518, where the repaired media is free of the artifact and at a similar quality to the input media.

A person having ordinary skill in the art can recognize that the digital media can be analog media converted to digital media, or media of a format that a neural network can process it.

FIG. 6 is a diagram illustrating an example embodiment 600 of an LSTM U-Net architecture. Each convolutional layer (e.g., cony layer) includes 3×3 convolutions while each LSTM layer uses 64 units. Applicant's system and method 600 performs 2×2 pooling and 2×2 upsampling, while also forwarding the feature map 610a-b from the contracting patch into the expanding path. A contracting path 602 reduces the size of the input image 606 while retaining the information necessary (e.g., feature maps 610a-b) to analyze the scene of the input image 606. The LTSMs process and remember that information in feature maps 610a-b over time. The expanding path 604 represents the neural networks restoring a larger version of the input image as the output image by using the feature maps 610a-b and forward connections.

In accordance with the above, accessibility can be thought of and processed in a sub-symbolic manner. Such sub-symbolic processing can enable learning to transform a visual scene into a form that is safer or clearer for a particular user. Previously, accessibility was largely treated as matter of extracting features, like objects, which are helpful for users rather than as a means to generally modify what is seen to make it more accessible. In general, Applicant's disclosure is a more flexible view of accessibility than the task-replacement paradigm, where machines essentially attempt to replace vision or other senses and provide the resulting information to humans rather than enable human senses to operate better, which dominates prior efforts, as described by Leo et al. (2017).

Next, Applicant's method can be applied to other problems, such as unlocking the content of faces for those who cannot easily perceive emotions. In doing so, Applicant demonstrates that these notions can be applied to other embodiments than solely just for correcting media for photosensitive seizure disorders.

For many people diagnosed with autism and other disorders, facial processing (e.g., of facial expressions/emotions) can be difficult. Often, difficulty processing faces is not due to visual impairment but instead because of the neural mechanisms behind face perception. The Stanford Autism Glass Project (Washington et al., 2016) demonstrates that highlighting facial expressions can be extremely useful and can even lead to learning to better recognize facial expressions in the real world. Traditionally, highlighting of facial expressions is performed manually.

In addition to manually annotating faces and their emotional valence, Applicant's disclosure can be employed to learn, with one or more neural network, to highlight the features which are important for most faces. Since those features are different for each face, each emotion, and as each emotion is being enacted, said learning is a dynamic process. However, the learning, generally, is similar to the photosensitivity application discussed early. Instead of removing flashes to enable one with photosensitivity to see the rest of a video, Applicant's system can highlight features to encourage a user to pay attention to those features. In other embodiments, Applicant's system can deemphasize or dull features that are not important, make important features bigger, make less important features smaller, or increase, decrease, or introduce contrast, resolution, or blur, etc. A person having ordinary skill in the art can recognize that any of the above can be used in conjunction or in isolation. This approach and the one being employed by the Stanford Autism Glass project are complimentary: the Stanford Autism Glass provides guidance and training to focus on certain facial features and associate them with mental states, while the present disclosure actively transforms all faces to always guide someone to the most important facial features for a particular emotion.

In this disclosure, the system employs a proxy for the visual system rather than generating a dataset directly. The proxy is a convolutional neural network that recognizes emotions because convolutional networks have been shown to approximate part of the human visual system with some fidelity (Yamins and DiCarlo, 2016). It therefore follows that the results of transforming an image to make it easier for a network to understand will similarly make it easier for humans to understand.

The system selects random images of human faces from the Japanese female facial expression (Lyons et al., 1998) dataset, and postprocesses them to create a distribution over the emotional content of each face using a convolutional network (Levi and Hassner, 2015). This network is pre-trained on the CASIA WebFace (Yi et al., 2014) dataset and fine-tuned on the Emotion Recognition in the Wild Challenge (Dhall et al., 2014). Then, an image-to-image network, analogous to the video ones described earlier, is trained to transform such faces. The network is a U-Net, as described in section 3.2.2, which receives an input image and learns to predict a sparse mask that selectively blurs that image. The objective function of the U-Net is to produce a peaked unimodal response in the distribution of the output of the emotion recognition network. In embodiments, the system can apply this method to video, real-time video, or other media. For example, networks can be applied to audio to highlight emotional affect for people who have difficulty distinguishing human tones of voice.

Learning to transform the visual environment is a new tool for accessibility building on prior experience with hand-crafted transformations like daltonization. Here, Applicant's system uses neural networks to automatically learn new visual transformations with the goal of increasing accessibility. The space of possible transformations for different populations is immense; for example, one could learn to transform text to help those with dyslexia or to subtly manage visual attention for someone with ADHD. Such technology may benefit everyone by subtly altering the visual environment making it more pleasant, more readily accessible, and less distracting—an effect known as the curb-cut effect where accessibility technologies can end up helping everyone.

Transformations can be further customized to different individuals, not just to disabilities or populations. This is particularly important because disabilities and impairments are heterogeneous: they are often not total, they differ in how they affect each individual, and are sometimes associated with other disorders. Rather than providing a small number of preprogrammed customization options, a human can assist with the learning process. An individual might be given a generated test to fine-tune the transformation to their particular needs and preferences. The fact that object detectors are easily fine-tuned to new datasets with few examples indicates that such a test can likely be short; moreover one need not go through an entire test to improve the transformation or even stop at any predetermined point. The system could further record the neural activity of users, for example by using EEG, and subtly adjust the transformation to enable them to read more quickly, be less confused, or have fewer EEG artifacts even when no overt reaction is apparent. Since this does not necessarily require user feedback, transformations trained in this way may be of use to those who cannot easily communicate their needs and preferences. In principle, such networks can continue to be trained through a lifetime and adapt to users as they change.

Figure 7:
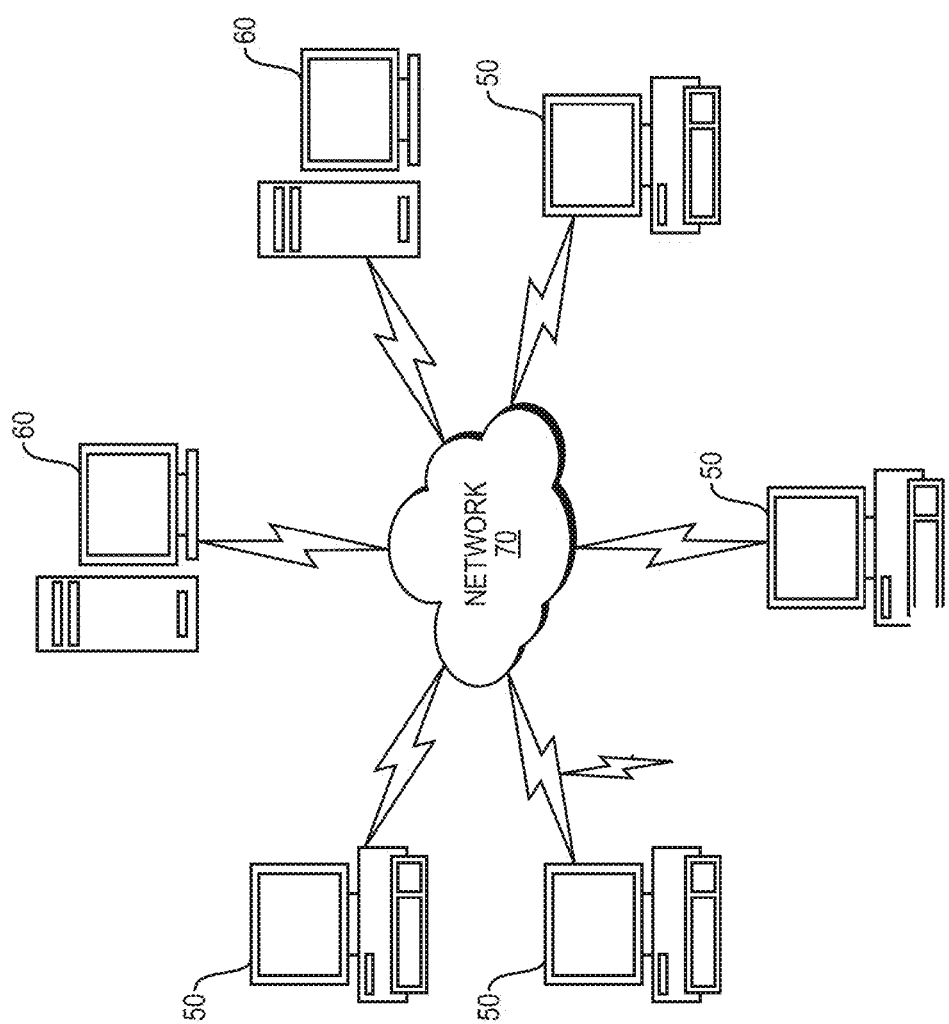
FIG. 7 illustrates a computer network or similar digital processing environment in which embodiments of the present invention may be implemented.

FIG. 7 illustrates a computer network or similar digital processing environment in which embodiments of the present invention may be implemented.

Client computer(s)/devices 50 and server computer(s) 60 provide processing, storage, and input/output devices executing application programs and the like. The client computer(s)/devices 50 can also be linked through communications network 70 to other computing devices, including other client devices/processes 50 and server computer(s) 60. The communications network 70 can be part of a remote access network, a global network (e.g., the Internet), a worldwide collection of computers, local area or wide area networks, and gateways that currently use respective protocols (TCP/IP, Bluetooth®, etc.) to communicate with one another. Other electronic device/computer network architectures are suitable.

Figure 8:
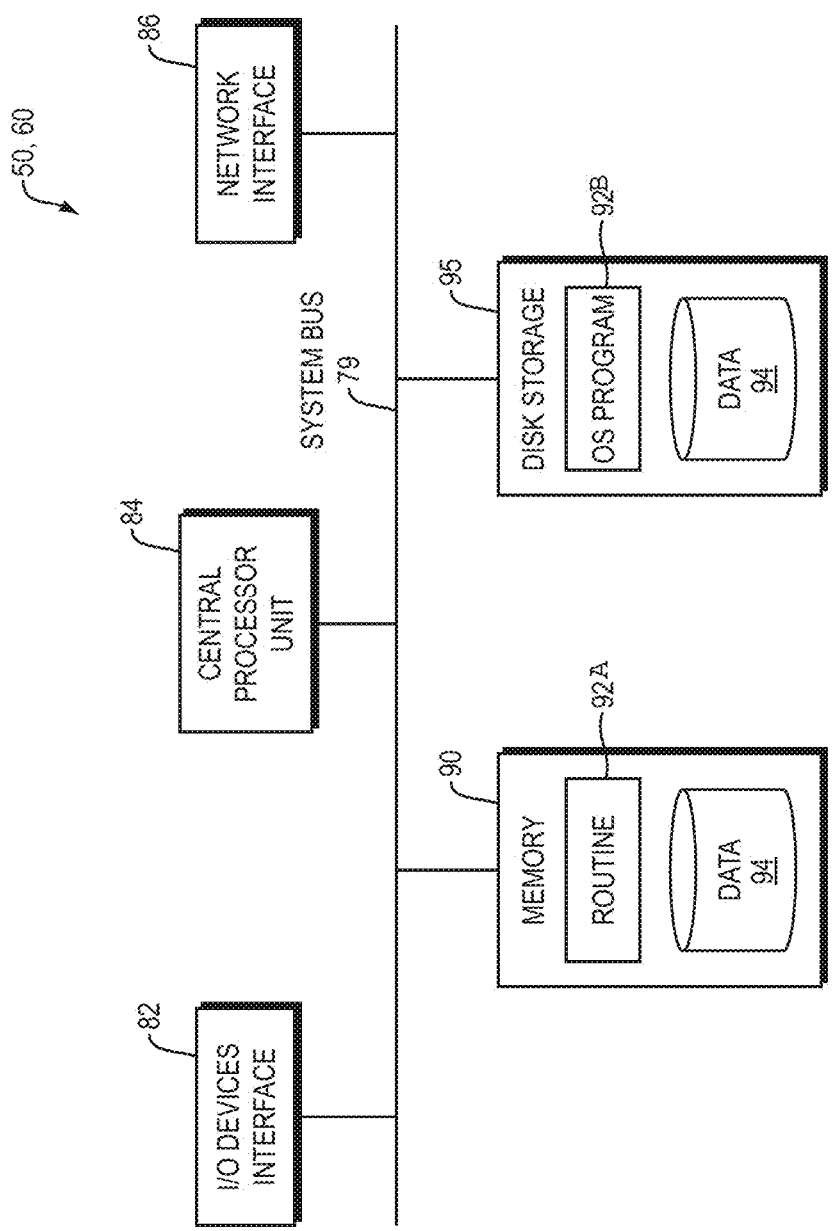
FIG. 8 is a diagram of an example internal structure of a computer (e.g., client processor/device or server computers) in the computer system of FIG. 7.

FIG. 8 is a diagram of an example internal structure of a computer (e.g., client processor/device 50 or server computers 60) in the computer system of FIG. 7. Each computer 50, 60 contains a system bus 79, where a bus is a set of hardware lines used for data transfer among the components of a computer or processing system. The system bus 79 is essentially a shared conduit that connects different elements of a computer system (e.g., processor, disk storage, memory, input/output ports, network ports, etc.) that enables the transfer of information between the elements. Attached to the system bus 79 is an I/O device interface 82 for connecting various input and output devices (e.g., keyboard, mouse, displays, printers, speakers, etc.) to the computer 50, 60. A network interface 86 allows the computer to connect to various other devices attached to a network (e.g., network 70 of FIG. 7). Memory 90 provides volatile storage for computer software instructions 92 and data 94 used to implement an embodiment of the present invention (e.g., transform module, desired filter/function generation module, trained desired filter/function module, generator module, neural network, detector module, physiological measurement module detailed above, throughout FIGS. 1A-6). Disk storage 95 provides non-volatile storage for computer software instructions 92 and data 94 used to implement an embodiment of the present invention. A central processor unit 84 is also attached to the system bus 79 and provides for the execution of computer instructions.

In one embodiment, the processor routines 92 and data 94 are a computer program product (generally referenced 92), including a non-transitory computer-readable medium (e.g., a removable storage medium such as one or more DVD-ROM's, CD-ROM's, diskettes, tapes, etc.) that provides at least a portion of the software instructions for the invention system. The computer program product 92 can be installed by any suitable software installation procedure, as is well known in the art. In another embodiment, at least a portion of the software instructions may also be downloaded over a cable communication and/or wireless connection. In other embodiments, the invention programs are a computer program propagated signal product embodied on a propagated signal on a propagation medium (e.g., a radio wave, an infrared wave, a laser wave, a sound wave, or an electrical wave propagated over a global network such as the Internet, or other network(s)). Such carrier medium or signals may be employed to provide at least a portion of the software instructions for the present invention routines/program 92.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A method comprising:
introducing an auxiliary transformation to a digital media by applying a transform function to the digital media, resulting in a transformed digital media that represents the digital media altered by the transform function;
evaluating the transformed digital media to generate a metric estimating a human or animal response to the transformed digital media altered by the introduced auxiliary transformation; and
training a machine learning model by learning a desired transformation function from the transformed digital media and the metric associated with the transformed digital media, the resulting machine learning model able to remove the auxiliary transformation from any digital media by applying the learned desired transformation function.

2. The method of claim 1, wherein the desired transformation function is an inverse function of the auxiliary transformation.

3. The method of claim 1, wherein introducing the auxiliary transformation further includes introducing a respective auxiliary transformation to each digital media of a collection of original digital media, resulting in a collection of transformed digital media by generating the auxiliary transformation with the auxiliary transform function.

4. The method of claim 1, wherein the auxiliary transform function is specified by a designer.

5. The method of claim 1, wherein the auxiliary transform function is learned by a second machine learning model.

6. The method of claim 1, wherein generating the metric estimating the human response to the transformed digital media includes employing a predefined function to estimate the human response based on the transformed media.

7. The method of claim 1, wherein generating the metric estimating the human response to the transformed digital media includes collecting at least one physiological measurement, behavioral measurement, or preference from at least one testing user experiencing the transformed digital media.

8. The method of claim 1, wherein generating the metric estimating the human response to the transformed digital media includes employing a second machine learning model that is trained as a proxy for a human physiological measurement or behavioral measurement.

9. The method of claim 1, wherein the media type of the collection of digital media is at least one of videos, images, audio, text, virtual reality scenes, augmented reality scenes, three-dimensional (3D) video, and 3D scenes.

10. The method of claim 1, wherein the auxiliary transformation is at least one of:
introduction of flashing, a modification of features representing emotions in an image or video, a highlighting of features representing emotions in an image or video, or an obscuring of features that are irrelevant to emotions in an image or video, highlighting or obscuring features in the media representing a distraction, highlighting a key behavior out of a sequence of actions, highlighting future behaviors for the user or other agents, highlighting features indicating social interactions, a modification of text, human annotations, and modification of audio features.

11. The method of claim 1, further comprising:
repairing a given media to a modified media by applying the desired function to the given media, wherein the modified media is generated by application of the desired function to cause a human response or physiological state estimated by a metric having a particular value.

12. The method of claim 11, further comprising:
adjusting the machine learning model based on further behavioral measurements, physiological measurements, or preferences from a user experiencing the modified media.

13. The method of claim 1, wherein the machine learning model is a neural network.

14. A system comprising:
a transformation module configured to an auxiliary transformation to a digital media by applying a transform function to the digital media, resulting in a transformed digital media that represents the digital media altered by the transform function;
an evaluation module configured to evaluate the transformed digital media to generate a metric estimating a human or animal response to the transformed digital media altered by the introduced auxiliary transformation; and
an inverse function generation module configured to train a machine learning model by learning a desired transformation function from the transformed digital media and the metric associated with the transformed digital media, the resulting machine learning model able to remove the auxiliary transformation from any digital media by applying the learned desired transformation function.

15. The system of claim 14, wherein the desired transformation function is an inverse function of the auxiliary transformation.

16. The system of claim 14, wherein introducing the auxiliary transformation further includes introducing a respective auxiliary transformation to each digital media of a collection of original digital media, resulting in a collection of transformed digital media by generating the auxiliary transformation with the auxiliary transform function.

17. The system of claim 14, wherein the auxiliary transform function is specified by a designer.

18. The system of claim 14, wherein the auxiliary transform function is learned by a second machine learning model.

19. The system of claim 14, wherein the evaluation metric is further configured to generate the metric estimating the human response to the transformed digital media by employing a predefined function to estimate the human response based on the transformed media.

20. The system of claim 14, wherein the evaluation metric is further configured to generate the metric estimating the human response to the transformed digital media includes collecting at least one physiological measurement, behavioral measurement, or preference from at least one testing user experiencing the transformed digital media.

21. The system of claim 14, wherein the transformation module is further configured to generate the metric estimating the human response to the transformed digital media by employing a second machine learning model that is trained as a proxy for a human physiological measurement or behavioral measurement.

22. The system of claim 14, wherein the media type of the collection of digital media is at least one of videos, images, audio, text, virtual reality scenes, augmented reality scenes, three-dimensional (3D) video, and 3D scenes.

23. The system of claim 14, wherein the auxiliary transformation is at least one of:
introduction of flashing, a modification of features representing emotions in an image or video, a highlighting of features representing emotions in an image or video, or an obscuring of features that are irrelevant to emotions in an image or video, highlighting or obscuring features in the media representing a distraction, highlighting a key out of a sequence of actions, highlighting future behaviors for the user or other agents, highlighting features indicating social interactions, a modification of text, human annotations, and modification of audio features.

24. The system of claim 14, further comprising:
a repair module configured to repair a given media to a modified media by applying the desired function to the given media, wherein the modified media is generated by application of the desired function to cause a human response estimated by a metric having a particular value.

25. The system of claim 24, further comprising:
adjusting the machine learning model based on further behavioral measurements, physiological measurements, or preferences from a user experiencing the modified media.

26. The system of claim 14, wherein the machine learning model is a neural network.

27. A non-transitory computer-readable medium configured to store instructions for training a machine learning model, the instructions, when loaded and executed by a processor, causes the processor to:
introduce an auxiliary transformation to a digital media by applying a transform function to the digital media, resulting in a transformed digital media that represents the digital media altered by the transform function;
evaluate the transformed digital media to generate a metric estimating a human or animal response to the transformed digital media altered by the introduced auxiliary transformation; and
train a machine learning model by learning a desired transformation function from the transformed digital media and the metric associated with the transformed digital media, the resulting machine learning model able to remove the auxiliary transformation from any digital media by applying the learned desired transformation function.

* * * * *